US00PP09603P

United States Patent [19]

Leue

[11] Patent Number: Plant 9,603

[45] Date of Patent: Jul. 9, 1996

[54] IMPATIENS PLANT NAMED 'SPARKLER ROSE'

[75] Inventor: Ellen F. Leue, West Chicago, Ill.

[73] Assignee: Geo. J. Ball, Inc., West Chicago, Ill.

[21] Appl. No.: 445,380

[22] Filed: May 19, 1995

[51] Int. Cl.[6] ..... A01H 5/00

[52] U.S. Cl. ..... Plt./87.6

[58] Field of Search ..... Plt./87.6

*Primary Examiner*—Howard J. Locker

*Attorney, Agent, or Firm*—Burns, Doane, Swecker & Mathis

[57] ABSTRACT

A new and distinct cultivar of Impatiens plant, botanically known as *Impatiens wallerana,* and named 'Sparkler Rose' is provided. This new cultivar was the result of a controlled breeding program wherein a plant desingated 464-1 (non-patented in the United States) was pollinated by a plant designated 481-2 (non-patented in the United States). The new cultivar is early blooming and forms in abundance attractive fully double bicolored blooms of rose and white. The foliage is medium green. The plant exhibits a good basal-branching character and exhibits a medium upright mounded growth habit.

1 Drawing Sheet

SUMMARY OF THE INVENTION

The present invention provides a new distinctive Impatiens plant, botanically known as *Impatiens wallerana,* and hereinafter referred to by the cultivar name 'Sparkler Rose'.

The new cultivar is the product of a planned breeding program. More specifically, the breeding program which resulted in the production of the new cultivar was carried out in a controlled environment during September, 1991 at Elburn, Ill., U.S.A. The female parent (i.e., the seed parent) was a plant designated 464-1 (non-patented in the United States) which exhibits single red flowers and dark green foliage. The male parent (i.e., the pollen parent) was a plant desingated 481-2 (non-patented in the United States) which exhibits cherry/rose semi-double flowers with medium green foliage. The parentage of the new cultivar can be summarized as follows:

464-1×481-2.

The seeds resulting from the above pollination were sown and plantlets were obtained which were physically and biologically different from each other. Selective study resulted in the identification of a single plant of the new cultivar. This plant had distinctive fully double bicolored blooms and initially was designated 774-2.

It was found that the new cultivar of the present invention:

(a) exhibits in abundance attractive bicolored blooms of rose and white,
(b) is early blooming,
(c) forms medium green foliage,
(d) exhibits a good basal-branching character, and
(e) exhibits a medium upright mounded growth habit.

Asexual reproduction of the new cultivar by stem cuttings taken during September, 1993 and during October, 1994, at Elburn, Ill., U.S.A., has demonstrated that the characteristics of the new cutivar as herein described are firmly fixed and are retained through successive generations of such asexual propagation.

The 'Sparkler Rose' cultivar has not been observed under all possible environmental conditions to date. Accordingly, it is possible that the phenotype may vary somewhat with variations in the environment, such as temperature, light intensity, and day length.

The originator is unaware of any commercial vegetatively propagated cultivar which is similar to the new 'Sparkler Rose' cultivar.

When plant material of the 'Sparkler Rose' cultivar is subjected to standard random amplified polymorphic DNA marker analysis (RAPD) using polymerase chain reaction (PCR) and a known unique set of DNA primers, it is found to exhibit a fingerprint map which confirms its genetic distinctiveness.

Plants of the new cultivar will be marketed under the FIESTA trademark by Geo. J. Ball, Inc.

BRIEF DESCRIPTION OF THE PHOTOGRAPHS

The accompanying photographs show the new 'Sparkler Rose' cultivar with colors being as nearly true as it is reasonably possible to make the same in color illustrations of this character. The plants were being grown in greenhouses at West Chicago, Ill., U.S.A.

DETAILED DESCRIPTION

Figure 1:
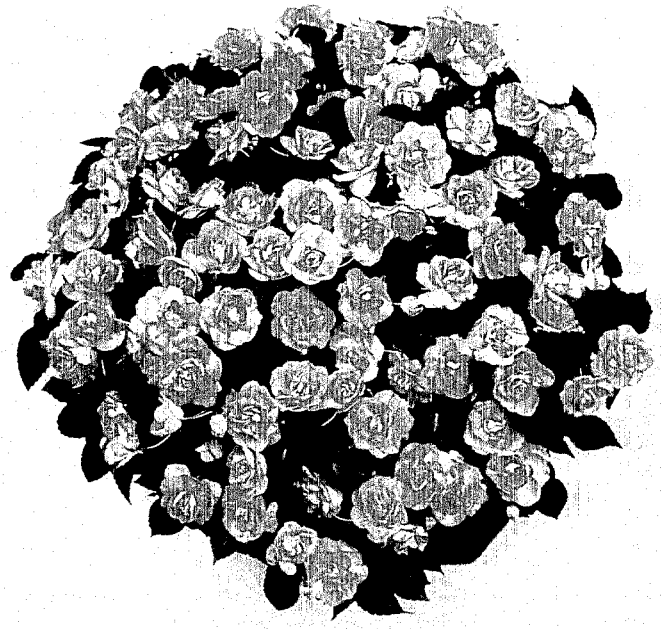
FIG. 1 illustrates the general appearance of an overall plant as seen primarily from above.
Figure 2:
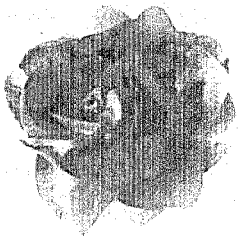
FIG. 2 illustrates the general appearance of a typical floret.

The chart used in the identification of colors described herein is the R.H.S. Colour Chart of The Royal Horticultural Society, London, England. The color values were determined on Jan. 3, 1995. The readings were taken between 10:00 and 11:00 a.m. under 2,000 footcandles of light at West Chicago, Ill., U.S.A. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type cutting.*—Two or three vegetative node stem cuttings from near the centers of the plants.

*Time to initiate roots.*—Approximately 7 to 14 days with the shorter times generally being experienced in the summer and the longer times in the winter.

*Rooting habit.*—Fibrous, and branching.

Plant description:

*Habit of growth.*—Basal-branching, and exhibits a medium upright mounded growth habit.

*Form.*—A mature plant at 8 weeks after the planting of a rooted cutting commonly measures approximately 13.0 to 18.0 cm. in height and approximately 21.0 to 26.0 cm, in width.

*Foliage.*—The configuration is ovate with an acuminate tip. The leaves of the new cultivar commonly measure approximatley 5.0 to 5.5 cm. in length and approximately 3.7 to 4.0 cm. in width. The foliage of the new cultivar is Green Group 137A (adaxial) and Green Group 137D with blotches of Greyed-Purple Group 185A (abaxial). The stem color is Yellow-Green Group 144C with streaks of Greyed-Purple Group 185A.

Flower description:

*Flowering habit.*—Freely flowering. Small round buds become more oval with maturity and flowers open in a rose-like fashion.

*Natural flowering season.*—Early blooming and blooms throughout the year in a greenhouse environment.

*Flowers borne.*—Slightly above the foliage.

*Flower color.*—Bicolored, Red-Purple Group 57A with irregular areas of white (adaxial), and Red Group 47D (abaxial). The white tends to be present at the tips of the petals.

*Quantity of flowers.*—Very floriferous. A mature plant commonly is totally covered with blooms.

*Number of petals.*—Fully double and the petals commonly are too numerous to readily count.

*Petal shape.*—Round to oblong.

*Flower size.*—Approximately 3.7 to 4.0 cm. in diameter.

*Spur.*—Approximately 2.8 to 2.9 cm. in length.

*Spur color*—Yellow-Green Group 144D.

*Reproductive organs.*—The stamens are multiple in number and the styles and ovaries are generally typical of the species and non-distinctive.

I claim:

1. A new and distinct cultivar of *Impatients wallerana* plant named 'Sparkler Rose' substantially as herein shown and described, which:

(a) exhibits in abundance attractive bicolored blooms of rose and white,
(b) is early blooming,
(c) forms medium green foliage,
(d) exhibits a good basal-branching character, and
(e) exhibits a medium upright mounded growth habit.

* * * * *